United States Patent
Bartsch et al.

(10) Patent No.: US 7,804,987 B2
(45) Date of Patent: Sep. 28, 2010

(54) METHOD AND APPARATUS FOR REPRESENTATION AND PREPARATION OF AT LEAST ONE EXAMINATION IMAGE OF AN EXAMINATION SUBJECT

(75) Inventors: Ernst Bartsch, Nürnberg (DE); Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1083 days.

(21) Appl. No.: 11/473,773

(22) Filed: Jun. 23, 2006

(65) Prior Publication Data
US 2007/0012881 A1 Jan. 18, 2007

(30) Foreign Application Priority Data
Jun. 23, 2005 (DE) ............. 10 2005 029 243

(51) Int. Cl.
*G06K 9/00* (2006.01)
(52) U.S. Cl. ................. 382/128; 382/100; 382/129; 382/131; 382/173; 382/224; 252/363.04; 600/424; 600/410
(58) Field of Classification Search .............. 382/100, 382/128, 129, 130, 131, 132, 133, 173, 224, 382/305; 600/424, 410; 128/899; 378/5; 715/700, 727, 733, 762; 250/363.04
See application file for complete search history.

(56) References Cited

U.S. PATENT DOCUMENTS

| | | | | |
|---|---|---|---|---|
| 5,644,232 A * | 7/1997 | Smith | ............... | 324/304 |
| 5,740,267 A | 4/1998 | Echerer et al. | | |
| 6,135,960 A | 10/2000 | Holmberg | | |
| 6,195,409 B1 | 2/2001 | Chang et al. | | |
| 6,480,619 B1 * | 11/2002 | Vuylsteke et al. | ............ | 382/132 |
| 6,529,758 B2 | 3/2003 | Shahidi | | |
| 6,574,296 B2 * | 6/2003 | Stierstorfer | ............. | 378/15 |
| 6,794,872 B2 * | 9/2004 | Meyer et al. | ............. | 324/318 |
| 7,450,747 B2 * | 11/2008 | Jabri et al. | ............. | 382/132 |
| 2002/0198447 A1 | 12/2002 | Van Muiswinkel et al. | | |
| 2003/0144589 A1 | 7/2003 | Roell | | |
| 2003/0214300 A1 * | 11/2003 | Bommel et al. | ............. | 324/318 |
| 2004/0078215 A1 | 4/2004 | Dahlin et al. | | |
| 2005/0010107 A1 | 1/2005 | Shen | | |
| 2005/0065617 A1 | 3/2005 | Moctezuma de la Barrera et al. | | |

FOREIGN PATENT DOCUMENTS

| | | |
|---|---|---|
| DE | 103 46 410 A1 | 5/2005 |
| EP | 0 429 148 A1 | 5/1991 |
| WO | WO 03/046810 | 6/2003 |

* cited by examiner

*Primary Examiner*—Samir A. Ahmed
*Assistant Examiner*—Ali Bayat
(74) *Attorney, Agent, or Firm*—Schiff Hardin LLP

(57) ABSTRACT

In a method and apparatus for representation and preparation of at least one examination image of an examination subject that is created with an imaging medical examination apparatus, the examination image is transmitted from the examination apparatus to a computer, and a whole-body coordinate system is specified with regard to the examination subject using at least one item of subject-specific information; and the examination image is spatially arranged in the whole-body coordinate system by the computer by means of the subject-specific information. At least one item of image information of the examination image is compared in the computer with the at least one item of subject-specific information of the whole-body coordinate system to check for consistency. The examination image is updated by the computer dependent on the comparison result and of the updated examination image is represented at an image reproduction device.

27 Claims, 3 Drawing Sheets

METHOD AND APPARATUS FOR REPRESENTATION AND PREPARATION OF AT LEAST ONE EXAMINATION IMAGE OF AN EXAMINATION SUBJECT

BACKGROUND OF THE INVENTION

1. Field of the Invention

The present invention concerns a method for representation and preparation of at least one examination image of an examination subject that is created with an imaging medical imaging apparatus.

2. Description of the Prior Art

If images of an examination subject are acquired with medical imaging apparatuses such as x-ray apparatuses or magnetic resonance tomography systems or the like, these must subsequently be prepared and shown in an intelligible form in order to enable an error-free evaluation by the doctor. For example, for this purpose it is necessary for the images to be shown in the correct orientation and with the necessary quality standards. For example, in the imaging of a limb for assessment of a fracture it is necessary for the entire fracture to be visible in the exposure and additionally to show the adjoining joints, possibly in at least two projection views. For this purpose, a manual quality assurance is implemented by a medical-technical assistant after the acquisition of the image, in which quality assurance the adherence to basic quality standards is checked. For example, it is established whether the exposures are associated with the correct patient specified on the exposures, whether the correct body part is imaged, etc. It is additionally checked whether the exposures are "readable" in the sense that they allow a diagnosis to be made as optimally as possible or an assessment with regard to the presence of a pathology and its severity.

The quality of such a preparation and subsequent representation as a "soft copy", thus for digital evaluation, is limited by the capability of the medical-technical assistant, his or her knowledge of possible representations desired by the evaluating doctor, and not least by errors given distraction or a lack of concentration. A problem additionally exists with regard to the efficiency of the workflow; it is not expected that a medical-technical assistant can or wants to prepare the data such that they are optimally adapted to the requirements for every single doctor who will evaluate these images afterwards. Post-processings are thus sometimes necessary or errors are not noticed at all since the preparation significantly depends on what, in a specific image, directly "catches the eye" of the competent technical employee. A high personnel requirement with simultaneously very high requirements for the training thus exists. At the same time, a non-negligible data traffic in the underlying network is necessary for such a preparation and in particular for a repeated preparation; the images are generally stored on a central server from which they must be recalled in order to be processed or post-processed by the technical assistants.

SUMMARY OF THE INVENTION

An object of the present invention is to provide a method and an apparatus of the aforementioned type that enable a qualitative representation and preparation of examination images with an improved workflow.

This object is achieved in accordance with the invention by a method wherein the examination image is transmitted from the examination apparatus to a computer, a whole-body coordinate system is specified with regard to the examination subject and with at least one item of subject-specific information, and the examination image is spatially arranged in the whole-body coordinate system by the computer by means of the subject-specific information, at least one item of image information of the examination image with is compared the at least one item of subject-specific information of the whole-body coordinate system to check the consistency, and the examination image is updated by the computer dependent on the comparison result and the updated examination image is presented at an image reproduction device.

The examination image generated with a medical examination apparatus (such as an x-ray apparatus or a ultrasound apparatus or the like) is initially transmitted to a medical-technical assistant to a corresponding specialized doctor (such as a radiologist who, for example, is active in a medical center or a center for image acquisition and processing) at a computer to which he or she has access. This transmission can ensue by means of a data connection, for example within a local network or over the Internet, or by means of a storage medium such as a CD-ROM. The receiving computer is normally a central server on which, for example, the data of all image acquisition apparatuses in a clinic are centrally stored. In this case, the examination image is initially cached by a control computer associated with the examination apparatus itself, with the control computer subsequently transfers the image to the central server. The computer can also be a server or workstation computer, for example of a center for processing medical images.

A whole-body coordinate system with regard to the examination subject is subsequently predetermined, meaning a coordinate system in which not only individual examination regions but also the entire body of the examination subject can be spatially arranged by the corresponding of coordinates. This whole-body coordinate system can already have been stored on a central server of the clinic or the like, or can be transmitted together with the examination image, or newly determined by using images or characteristic anatomical points of the examination subject. The coordinate system is based on subject-specific information such as the position of anatomical points or areas or the localization of boundary surfaces or lines, for example of specific organs in the body of the examined person or animal. In this whole-body coordinate system that is specific to the respective examination subject, the examination image, now newly generated and possibly to be prepared with the medical examination apparatus, is spatially arranged using the (at least one) item of subject-specific information of the whole-body coordinate system. For example, the position of the head can be known from the whole-body coordinate system, such that exposures from the neck/head region can be arranged in the (for example two- or three-dimensional) whole-body coordinate system using this subject-specific information by corresponding coordinates being associated with the images.

A comparison of at least one item of image information of the examination image with the at least one item of subject-specific information of the whole-body coordinate system is subsequently implemented in order to check the consistency of the existing information. It is normally reasonable to draw upon multiple items of image information for the comparison, for example the position of the right arm in addition to the position of the head, such that (for example given a head exposure from which the position of the right half of the brain arises) this information, together with the information of the position of the head and also the orientation information that results from the position of the right arm, can be used in order to detect medical errors. For example, a discrepancy between the whole-body coordinate system and the examination image can arise given the association of the right and left body halves, which discrepancy possibly requires an alteration of the representation of the examination image (such as a mirroring). Similarly, it can be detected via the comparison if an image initially associated with the head region does not include an item of characteristic image information, such as the eye socket.

A comparison of size information or the position of a number of anatomical points as information of the whole-body coordinate system and of the examination image enables the detection of an incorrect representation scale or also the association with an incorrect patient when full-scale deviations are not present.

Depending on the result to which the comparison leads, thus whether an error or a lack of consistency possibly exists in the present image information, an updating of the examination image ensues by the computer, and a representation of the updated examination image ensues on an image reproduction device such as a display or monitor or the like. If no error with regard to the subject-specific image information was detected in the check of the examination image arranged in the coordinate system, the "updating" merely represents an unchanged storage, and the image can, if applicable, be shown in the form as it was originally present.

Errors are thus automatically detected and corrected, and an automatic preparation ensues for the digital readout of the image for evaluation by the doctor. The portion of the detected medical errors is increased by the use of an automatic method on the basis of a whole-body coordinate system. The method can, if applicable, run entirely on a server without additional data traffic between the server and various workstation computers, or an interactive task on a workstation computer, being necessary.

Furthermore, in accordance with the invention the computer transmits at least one item of standard information for the examination image (in particular the acquisition time and/or the acquisition region and/or the examination position and/or a medical coding and/or the name of the examination subject), and a comparison of at least one item of image information of the examination image with the standard information is undertaken and, if applicable, a correction of the standard information is implemented.

For example, it is possible that an image of the cervical spinal column is generated with an x-ray apparatus for a patient with problems of the cervical spinal column. In general, such images are stored with a "header" that includes standardized information. For example, if the acquisition region is in the header in addition to the acquisition time but is incorrectly specified as the thoracic spinal column, the comparison of the header content with image information of the examination image by means of the computer (for example with regard to the position or also only to the presence of a specific vertebra) detects that the image does not show the thoracic spinal column as specified. With a corresponding program that can access information sources such as medical databanks, an item of image information of the examination image can be correctly associated, for example as a position of a cervical vertebra, and the standard information about the acquisition region can be correspondingly corrected.

The same applies for the case that an incorrect examination position and/or an incorrect examination was specified; the image exposures are characteristic both for the position of the patient and for the respective apparatus, such that corrections can be effected or at least an error output can be generated with a program. Such an error output is necessary when the exposure is complicated to interpret or is rare, or when, after a consideration of multiple items of standard information, such a significant discrepancy exists between these specifications and the examination image so that a correction is not possible.

It is also possible for an incorrect medical coding to be associated with the image exposure, for example a coding for an exposure indicating the prior administration of contrast agent that does not appear from the information of the examination image, such that it can be deduced that no contrast agent administration occurred. A simple check, for example using gender-specific image information, is possible by the specification of the name of the examination subject. Such an error in the specification of the standard information normally can be corrected only when further information exists beyond an examination image, for example a series of examination images with a correctly-associated patient name, or comparison images that correspond to earlier exposures, using which it can be identified with which patient this image is to be associated.

Furthermore, in addition to the whole-body coordinate system the computer can predetermine at least one representation (display) request for the examination image, and a comparison of at least one item of the examination image with the representation request can be implemented. Such a representation request can be adapted to the personal viewing preferences of the respective radiologist or other doctor who must create a report using the images. In addition to this, the representation request can concern the representation of the individual examination image together with a series of further images, for example a representation in an examination image or at a predetermined position of an image series that is anatomically aligned in a predetermined manner, for example such that the images are arranged from the right half of the body of the patient to the left in this order. Given the comparison of the representation request, as with a comparison with regard to the standard information as well as the to the subject-specific information of the whole-body coordinate system it is also meaningful for the corresponding doctor or medical-technical assistant to be informed about the comparison result and/or the images are provided with information regarding corrected medical errors in order to be able to detect a frequently-occurring error in the image acquisition, and to be able to check the work of the automatic error recognition so that new errors are not introduced into the method of the image preparation in this manner. It is likewise useful for the image representation to ensue with short specifications regarding the respective processes.

In accordance with the invention the size and/or the scale and/or the position and/or the orientation of the examination image can be predetermined as a representation request. For example, for the assessment of an image series it can be advantageous when the size is fixed, such that the images are displayed on the screen in a uniform series of the same size. In contrast to this, for the assessment of pathological variations it is useful for the scale to be predetermined such that, given a representation of two images, of which one was acquired earlier from the same examination region, an enlargement or reduction of a tumor can be detected immediately. It can additionally be useful to predetermine the position and/or the orientation of the examination image. For this purpose anatomical specifications can be used with regard to the directions in the body or with regard to the position of specific examination regions. An image thus can be displayed at the anatomically correct position in a whole-body image. At the same time it can also be checked whether a patient has assumed the correct positioning (for example lying on his or her side) during the acquisition of the image, such that the created image was actually acquired in the desired position.

Furthermore, in accordance with the invention a quality standard for the examination image is provided to the computer in addition to the whole-body coordinate system, and a comparison of at least one item of image information of the examination image with the quality standard is implemented. For example, for an examination of the cervical spinal column the quality standard can be a predetermination that the entire cervical spinal column region should be visible in the exposure or that the cervical spinal column region should be visible such that a good differentiation of the individual vertebrae is possible. Together with the original consideration of the information of the whole-body coordinate system, the comparison makes quality standards into account as well as representation requests, and standard information is used for the updating and representation of the examination image, such that various specifications are incorporated into the actual image representation.

According to the invention, requirements of the image content and/or the imaging quality and/or imaging type can be predetermined as the quality standard, for example in the case of a fracture, the entire fracture should be visible as well as possible adjoining joints. The imaging quality can also be determined in advance as a specification for the contrast or the brightness or the like. Specific settings in the examination apparatus that is used for image acquisition can be predetermined by the imaging type. For example, it can be predetermined that only one scan image should be acquired that shows a larger examination region, or that a detail acquisition with a specific, predetermined setting is desired. If the comparison produces the result that such specifications are not fulfilled, the image can, if applicable, be discarded in the context of the updating and, instead of this, an error message can be shown when a correction is not possible.

An anatomical marker of the body of the examination subject and/or the position of further markers and/or an overview image of the examination subject, the anatomical marker being associated with the origin, can be predetermined as an item of subject-specific information. For example, it is possible that the coordinate system was established using a specific vertebra of the patient that forms the origin of the coordinate system. Additionally or alternatively, the position of further markers (such as, for example, the back prominences can be present as subject-specific information in the coordinate system, thus in the form of the corresponding coordinate specification. The image information can also be the position of an overview image of the examination subject in the coordinate system, for example merely the contour lines or an overview image with marked points. For example, if the contour lines of an overview image are available, by a comparison of their image information with the contour lines of the overview image examination, images of many different body regions can be easily updated or corrected with regard to underlying errors such as an incorrectly-specified orientation.

According to the invention, the size and/or the scale and/or the position and/or the orientation of the examination image can also be compared. These items of image information can be used both for the comparison with the subject-specific information and for the comparison with representation request, the standard information and the quality standard. Given a comparison with the information regarding the coordinate system, a consideration of size and scale can indicate that completely different proportions result from the examination image than would be possible using the coordinate system, for which, for example, an overview image is known. This indicates that the examination image is not to be associated with the same patient as the coordinate system. The adherence to representation requests can additionally be directly checked using the size and the scale as well as using the position and the orientation.

It is particularly advantageous to implement a fusion with at least one further examination image in the updating of the examination image. Images of adjoining regions can thus be fused into an overview image of a larger region in order to be more easily visually recognizable. The existing correlation can be shown to the doctor for information, for example via an additional text output or via a representation of the contour lines of the various examination images that were used for the representation. Naturally, more than two examination images can be fused, for example in order to obtain a three-dimensional view on the basis of two-dimensional images.

The examination image can be fused with an examination image of another examination apparatus. For example, the image of a magnetic resonance examination can be fused with the image of a computed tomography apparatus or an ultrasound apparatus in order to obtain image information characteristic of different acquisition techniques in a single image. The use of the whole-body coordinate system, which allows a problem-free arrangement of the images of different examination apparatuses in a single, patient-specific coordinate system, is significant for this purpose, such that a direct comparability of the shown regions is presented. A fusion of images of different acquisition modalities that acquire different examination regions of the patient is thereby also possible, such that ultimately a complete overview image with adjoining regions is created.

According to the invention, in the updating of the examination image at least one transformation (in particular a size change and/or a rotation and/or a mirroring and/or a displacement) can be implemented. A specific representation request thus can be satisfied by a size change, while a rotation can compensate possible errors in the positioning in comparison with the information of a whole-body coordinate system. A mirroring can be reasonable when it is determined from the standard information that the image exists exactly inverted. Inconsistencies after the first arrangement of the examination image in the whole-body coordinate system can be remedied by a displacement, such that the examination image appears at the correct point given an overview representation together with other images, for example for representation of a slice through the entire body.

According to the invention, the representation of the updated examination image can ensue dependent on the updating of other examination images and/or together with other examination images. The image thus can be shown in a series together with other examination images, whereby the images can be arranged such that the order is anatomically meaningful, for example proceeding from the head region into the thoracic region with regard to the image contents. The updating (and therewith the representation of an individual image) can be postponed until further images have been transmitted and checked in order to obtain therefrom new information to allow, for example, an evaluation of whether an incorrect scale of the image representation actually exists that does not correspond to that desired. This results, for example, by a comparison with the remaining examination images when these show the correct scale and a corresponding adaptation of the first image appears necessary so that the anatomical proportions are consistent overall.

Furthermore, dependent on the comparison result, the examination image can be associated with a billing code in order to simplify the generation of a cost accounting. For example, given an examination image in which no errors were detected in connection with the implemented comparisons with regard to the coordinate system as well as the predetermined standards or standard information, the billing code to be associated with the examination (which, among other things, arises from the standard information) can be automatically specified for an automatic calculation. The association of the billing code can also ensue dependent on whether a specific quality standard (which can be connected with different billing codes) was adhered to.

Moreover, the computer can compare the examination image and/or the standard information and/or the whole-body coordinate system and/or the representation request and/or the quality standard with rules stored in the storage unit, in particular a databank. These rules can be, for example, rules of an expert system (neural network) that, on the basis of expert knowledge, supply instructions for evaluation or regarding possible problems in connection with the existing information. These rules can be derived from preceding examinations, from determined realizations given the manual arrangement and representation of images, or they can be rules from dictionary-like knowledge collections such as, for example, an anatomical atlas. These rules can also contain specific correlations, for example between a representation request and the quality standard, such that an error message is generated when, given a specific representation type, the predetermined quality cannot be achieved at all for anatomical or technical acquisition reasons. For example, given a specific positioning of the patient for the acquisition it may be impossible to show the joints adjoining a bone in an image. Tomography imaging would be detected and, if applicable, reported by a comparison with the corresponding databank rules. The examination image, together with the standard information of the shown examination region, can likewise be compared with corresponding rules with regard to that which should or could be visible in such an image of the examination region. Anatomical peculiarities that are possible in individual cases can also be taken into account insofar as these are present in special rules, for example extracted from a lexicon.

An action, in particular the output (prompt) of an input requirement for a user, can be effected dependent on the comparison result. The medical-technical assistant thus can be informed that a specific quality standard was not achieved since the corresponding rules of the databank are not fulfilled. At the same time, the medical-technical assistant can be informed that this quality standard cannot be met given the orientation that corresponds to the representation request. The operator can be requested to acknowledge the notice of this message or to input a specific change to the representation request, or even to discard the exposure. For example, the standard information about the acquisition time can analogously be compared with rules of the databank that typically concern acquisition times in order to be able, for example, to detect that an examination has taken a particularly long time. This can be displayed to the operator, who can thereupon decide whether the time specification could be incorrect or specific problems existed in the image acquisition about which he or she would have to be informed.

Furthermore, according to the invention the updating of the examination image and/or the representation of the examination image can be acknowledged and/or revised by a user.

For example, an adaptation of the size of the image can be displayed, the user can either acknowledge this or cancel it when he or she does not deem it to expedient, for example, if resolution problems occur. It is also possible to give the user the option of merely revising updates, for example, by an adaptation of the scale that was effected not being entirely cancelled, but instead an adaptation is selected that involves smaller changes. In connection with the acknowledgement or the discarding of the update, correlations (for example between images of different examination apparatuses) can also be shown to the user so that the user can decide, using the relation between the images, whether the update should be implemented or not.

A user can interact with the computer via a user interface, in particular by means of an input device such as a keyboard and/or a mouse. Inputs can be implemented with the keyboard, for example by a parameter of an update being corrected to a different value. A transformation that should be implemented in the examination image can likewise be adapted with the aid of the mouse pointer by, for example, the user shifting the examination image to the screen position provided for representation. The input device also can serve to input quality standards or representation requests as well as further additional standard information.

The computer can inventively check the authorization and/or a login of a user and/or establish the user rights according to the position of the user. Thus an unauthorized user can be prevented from affecting an update and therewith possibly a deletion of original image data that would then be lost for a further preparation. It is additionally prevented that unauthorized persons have access to patient data. The user rights can be established dependent on the login or the authorization that can be connected with a corresponding group association. For example, it can be permitted that acquisition images can be deleted or be overwritten with updated images by a specific category of persons, while a different group only has access to specific examination images of a specific modality or of a specific patient.

The processing of the examination image for graphical representation and the other data processing can be implemented in different modules of the computer. The graphical representation thus can occur independently of the other data processing such as, for example, the association of medical codes with the images, such that, for example, the graphical representation can be interrupted when errors that can appear to demand a termination are found in the framework of the other data processing, such as the checking of the standard information. The generally longer time for graphical processes (such as, for example, rendering) is therewith taken into account so that unnecessary computer power is not used. The module distribution furthermore enables a graphical representation to possibly be wholly foregone, if this should ensue only in a later work step.

The invention concerns an apparatus for representation and preparation of at least one examination image of an examination subject that was generated with an imaging medical examination apparatus, the apparatus being designed for implementation of the method as described above.

DESCRIPTION OF THE PREFERRED EMBODIMENTS

Figure 1:
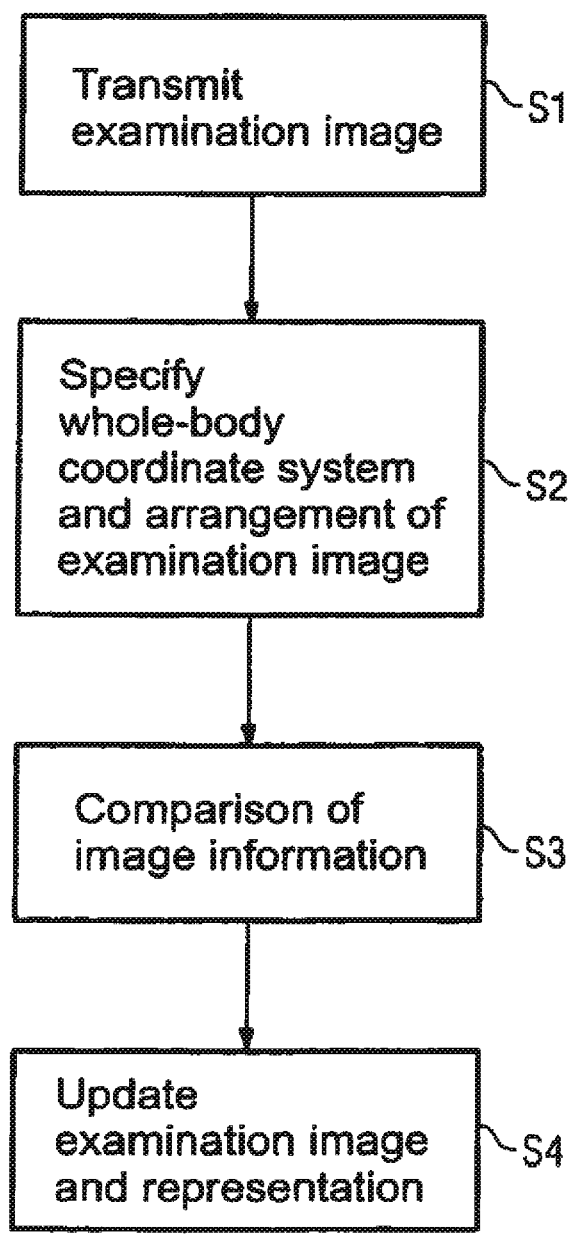
FIG. 1 shows the workflow of an embodiment of the inventive method.

FIG. 1 shows the workflow of an embodiment of the inventive method. In step S1 of the inventive method for representation and preparation of at least one examination image created with an imaging medical examination apparatus, the examination image is initially transmitted from the examination apparatus (for example a computed tomography apparatus or a ultrasound apparatus) to a computer. This can ensue via a data connection, possibly via the associated control device of the examination apparatus. It is also possible for the transmission of the examination image to ensue with the aid of storage media such as diskettes or CD-ROMs or the like.

In step S2, a whole-body coordinate system is then predetermined that is related to the body of the examination subject (which can be a patient or an animal). The whole-body coordinate system includes at least one item of subject-specific information, for example the position of the origin point as an anatomical specification, or the position of the contour lines of the body or specific organs thereof, using which information the arrangement of the examination image in the whole-body coordinate system ensues. This spatial arrangement means that corresponding coordinates of the whole-body coordinate system are associated with the examination image. For example, a corresponding coordinate region of the whole-body coordinate system can be associated with an exposure of the head insofar as the head region is situated within the coordinate system, or would have to be situated within the coordinate system according to the subject-specific information.

A comparison of at least one item of image information of the examination image with the at least one item of subject-specific information of the coordinate system occurs in step S3. For example, in the case of a head exposure an actual item of image information of the examination image can now additionally be used such as, for example, the position of the eye sockets or the nasal bone or the jawbone. This image information can be provided with specific coordinates using the spatial arrangement implemented in the preceding step, such that a comparison with subject-specific information of the whole-body coordinate system is possible. An inconsistency can result from this comparison when, for example, an actual item of image information present on the examination image in this coordinate region is not head-specific information at all, but rather image information of an extremity. In this case, a medical error is detected and output as an inconsistency.

The updating of the examination occurs in step S4 dependent on the comparison result as well as the representation of the updated examination image on an image reproduction device (such as a monitor), possibly after a corresponding affirmation of an operator of the computer. In the case of the preceding error example, such an update can be implemented by the image (which was, for example, arranged as a head image based on associated standard information) being shifted until the position thereof actually corresponds to the position of the shown extremity in the whole-body coordinate system. For the updating it is helpful when additional further standard information that exists with regard to the examination image is used so that the inconsistency can be better evaluated. In addition, predetermined representation requests or quality standards can be used. If applicable, a check is possible using rules of an expert system.

Figure 2:
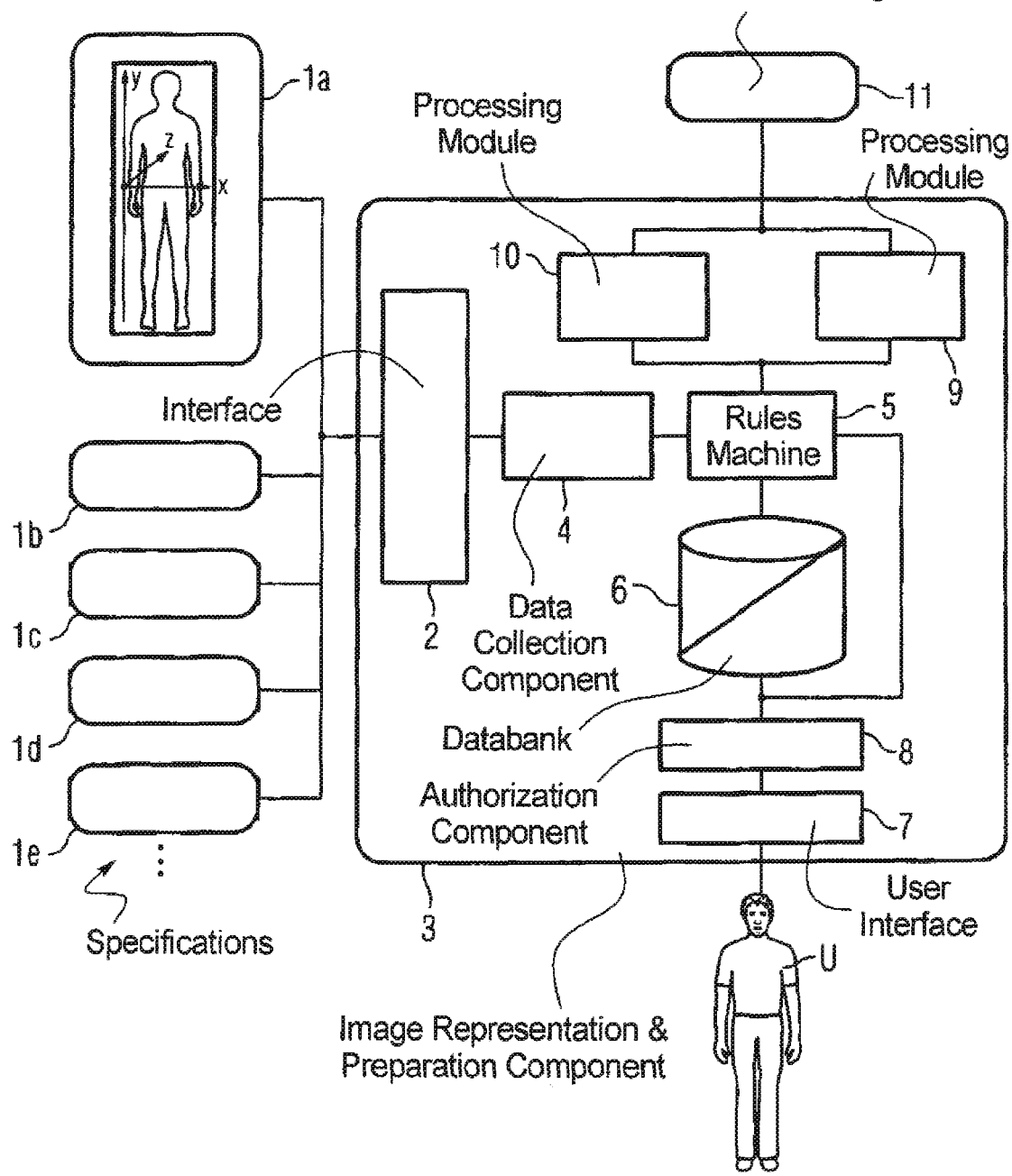
FIG. 2 shows the interaction of components in the workflow of the inventive method.

FIG. 2 shows the interaction of components in the workflow of an inventive system. The computer hereby initially receives different specifications $1a$-$1e$, whereby the specification $1a$ is the whole-body coordinate system. The specification $1b$ shows a representation request, $1c$ a quality standard and $1d$ standard information that exists in a "header" with regard to the respective examination image. Finally, the examination image that should now be prepared and represented as well as further examination images that were acquired with the same examination apparatus or a different examination apparatus are designated with the specification $1e$. These different examination images are transmitted from the control devices of the respective examination apparatuses to a central server. The specifications $1a$-$1e$ are transferred by means of an interface 2 of the representation and preparation component 3. The data acquired from the interface 2 are ultimately forwarded to the data collection component 4 that collects the data as they exist from the specifications $1a$-$1e$, thus both image data and quality specifications and the like. A rules machine 5 effects a comparison of the data from the specifications $1a$-$1e$, thus for example of the examination image and the representation request, with rules specified in a databank 6. All relevant rules with regard to the representation request or standard rules for the image quality or correct association rules for the positioning as well as the standard information of the "header" are stored in the databank 6. In the event that the rules machine 5 discovers discrepancies in its comparison, it executes the actions corresponding to the specifications predetermined beforehand by a user U. Specific, predetermined actions that are not user-specific can also supersede the specifications of the user U (who will normally be a medical-technical assistant). The optimization of the workflow in the clinical field and the correction as well as detection of medical errors are in the foreground in the rule set that is accessed.

User inputs of the user U ensue via a user interface 7 that, for example, serves for input of a login, for acknowledgement of automated corrections, for revising (for example in the sense of a fine tuning) etc. Via the user interface 7 it is likewise possible that the user U can set specific, suitable triggers that should invoke a specific action in the inventive method. The user U can likewise provide rules that can be stored in the databank 6 for specification of the automatic actions in the inventive method. The check of the authorization of the user as well as the implementation of the login procedure ensues via the authentication and authorization component 8, whereby the user U receives rights that correspond to his association with a specific group. A radiologist will thus be allocated different rights than a medical-technical assistant or an administration of the device. The processing module 9 serves for the processing of the examination image for graphical representation while the processing module 10 has the task of the other data processing for the computer. The actual image processing, and in particular the rendering in order to obtain the images in the desired representation, ensues in the processing module 9. In contrast to this, the processing module 10 serves to implement the other data processing such as, for example, the association of medical encodings and the like. Finally, the updated examination image 11 is shown at the end of the method on an image reproduction device after a corresponding check of the existing standard information and corresponding to the desires with regard to the representation, the predetermined quality requirements and the specifications of the whole-body coordinate system.

Figure 3:
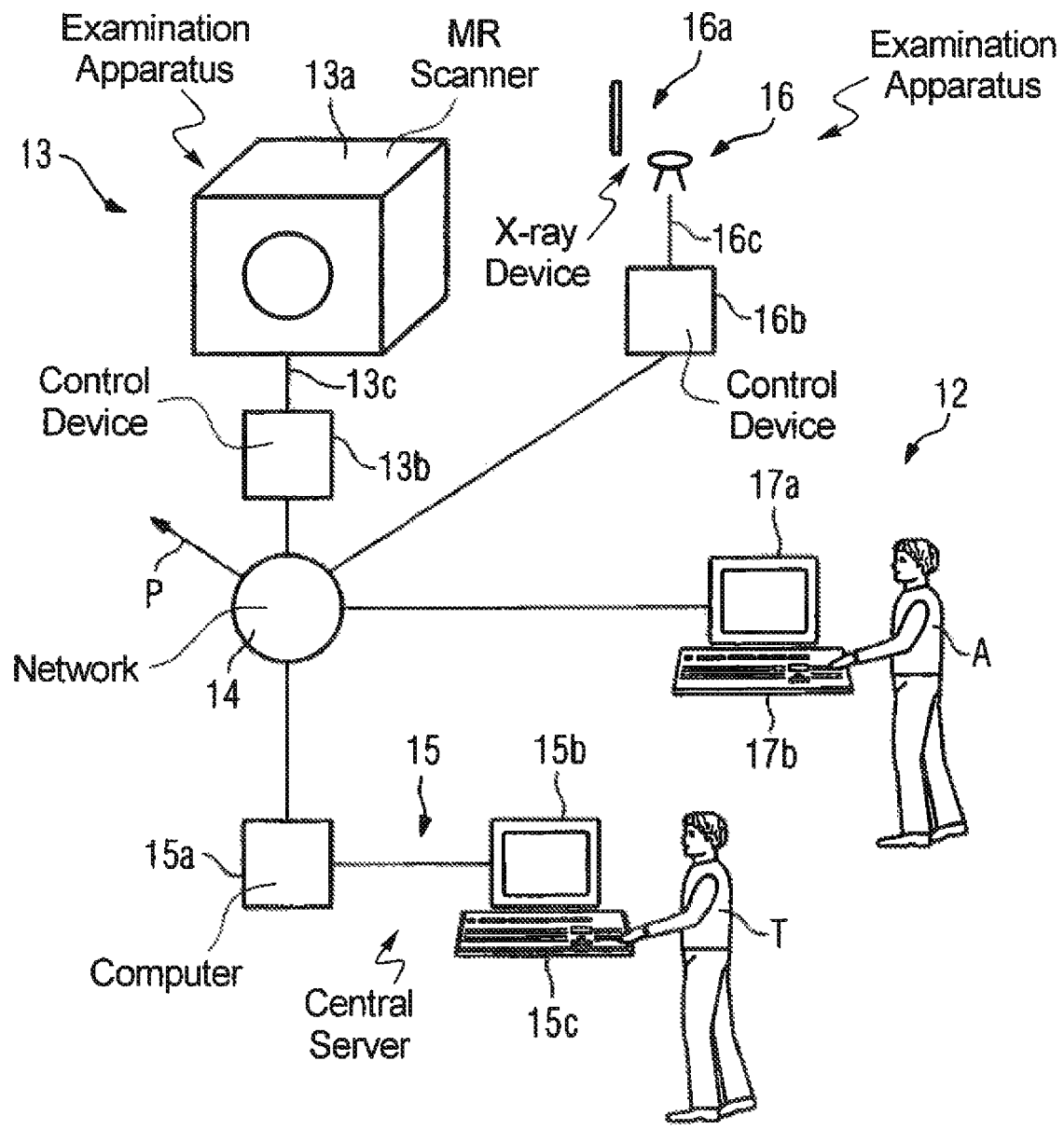
FIG. 3 shows an inventive apparatus.

FIG. 3 shows an inventive apparatus 12 for representation and preparation of examination images generated with medical examination apparatuses. An examination image is initially created with the examination apparatus 13, a magnetic resonance apparatus. The examination image is acquired in the magnetic resonance scanner $13a$ after corresponding specifications have been transmitted from the control device $13b$ via the data connection $13c$. The examination image of the magnetic resonance scanner $13a$ is subsequently transmitted to the control device $13b$, which has a storage device. The examination image suitable for further preparation is subsequently transferred over the network 14 to a central server device 15. The central server device 15 has a computer $15a$ as well as an image reproduction device $15b$ (connected with the computer $15a$) with an associated input device $15c$.

Furthermore, the examination apparatus 16, composed of an x-ray device 16a as well as an associated control device 16b that are connected with one another via a data connection 16c, is connected to the server device 15. Examination images are also created with the examination apparatus 16 and transmitted over the network 14 to the server device 15. A whole-body coordinate system (relating to the examination subject) with at least one item of subject-specific information exists on the server side. The subject-specific information can also be an overview image that was created by one of the examination apparatuses 13 or 16 or a further examination apparatus to which a connection likewise exists via the network 14 (indicated here by the arrow P). The computer 15a of the server device 15 effects the spatial arrangement of the examination images of the examination apparatuses 13, 16 in the whole-body coordinate system in that the subject-specific information of the coordinate system is used.

Image information of the examination images are subsequently compared with subject-specific information of the whole-body coordinate system (such as, for example, anatomical markers present at the corresponding coordinates) in order to check the consistency between the information of the whole-body coordinate system and the image information. An updating of the examination image subsequently occurs dependent on the comparison result, and the computer 15a effects the representation of the examination image by means of the image reproduction device 15b. The representation on the image reproduction device 17a that belongs to the workstation of a doctor A can likewise be effected. The doctor A has (via an input device 17b) specific possibilities for interaction, for example in order to adapt the images to be shown. A preceding acknowledgement or, respectively, revision of the representation of the examination image can be performed by the medical-technical assistant who for this affects corresponding inputs via the input device 15c. Given the updating of the examination image, a fusion of the examination images of the different examination apparatuses 13 and 16 can also be implemented.

Overall, with the inventive apparatus 12 allows an automated error detection and (if applicable) correction in addition to an optimization of the workflow and an increase of the work efficiency, in that systematic specifications for the preparation and representation of the images are acquired and checked. The quality assurance is implemented automatically, and the examination images are brought into a digitally-readable form according to the specifications made. The medical-technical assistant is supported in his or her work by being relieved of specific details of the work, and specific tasks run automatically. The medical-technical assistant can thus gain time and concentrate on tasks for which his or her intervention is necessary, for example clearing up errors that cannot be corrected automatically or finding compromises when irreconcilable specifications conflict with one another.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for representation and preparation of at least one examination image of an examination subject that is produced with a medical imaging apparatus, comprising the steps of:

transmitting the examination image from the imaging apparatus to a computer;

in said computer, specifying a whole-body coordinate system with regard to the examination subject and including at least one item of subject-specific information, and electronically spatially arranging the examination image in the whole-body coordinate system dependent on the subject-specific information to obtain a spatially-arranged examination image;

checking for consistency between said subject-specific information and said spatially arranged examination image by, in said computer, comparing at least one item of image information representing a feature depicted in the spatially arranged examination image with said at least one item of subject-specific information of the whole-body coordinate system, and thereby obtaining a comparison result that indicates whether an inconsistency exists between said item of image information and said at least one item of subject-specific information; and when said comparison result indicates said inconsistency, automatically updating the examination image in the computer dependent on the comparison result to remove said inconsistency, and electronically representing the updated examination image at an image reproduction device.

2. A method as claimed in claim 1 comprising, through said computer, accessing at least one item of standard information for the examination image, selected from the group consisting of an acquisition time, an acquisition region, an examination position, an associated examination apparatus, a medical coding and a name of the examination subject, and using said at least one item of standard information as said at least one item of image information for comparison with said at least one item of subject-specific information and, if said comparison result indicates a lack of consistency between said at least one item of standard information and said at least one item of subject-specific information, correcting said at least one item of standard information.

3. A method as claimed in claim 2 comprising, in said computer, comparing said at least one item of image information of the examination image with at least one item of standard information using rules stored in a storage unit accessible by said computer.

4. A method as claimed in claim 3 comprising emitting a user prompt dependent on said comparison result.

5. A method as claimed in claim 1 comprising entering at least one representation request defining representation of said updated examination image at said image reproduction device, and, in said computer, additionally comparing said at least one item of image information of the examination image with said representation request.

6. A method as claimed in claim 5 comprising, in said computer, comparing said at least one item of image information of the examination image with said representation request using rules stored in a storage unit accessible by said computer.

7. A method as claimed in claim 6 comprising emitting a user prompt dependent on said comparison result.

8. A method as claimed in claim 5 comprising entering said representation request as a request selected from the group consisting of a size of the representation of said updated image at said image reproduction device, a scale of the representation of said updated image at said image reproduction device, a position of the representation of said updated image at said image reproduction device, and an orientation of the representation of said updated image at said image reproduction device.

9. A method as claimed in claim 1 comprising entering a quality standard for said examination image into said computer and, in said computer, additionally comparing said at least one item of image information of the examination image with said quality standard.

10. A method as claimed in claim 9 comprising, in said computer, comparing said at least one item of image information of the examination image with at least one item of quality standard using rules stored in a storage unit accessible by said computer.

11. A method as claimed in claim 9 comprising entering said quality standard as at least one entry from the group consisting of the image content, imaging quality, and imaging type.

12. A method as claimed in claim 1 comprising emitting a user prompt dependent on said comparison result.

13. A method as claimed in claim 1 comprising providing, as said subject-specific information, to said computer information selected from the group consisting of an anatomical marker of the body of the examination subject, associated with an origin of said whole-body coordinate system, a position of additional markers, and an overview image of the examination subject.

14. A method as claimed in claim 1 wherein the step of comparing at least one item of image information of the examination image with said at least one item of subject-specific information includes comparing at least one of a size of the examination image, a scale of the examination image, a position of the examination image and an orientation of the examination image.

15. A method as claimed in claim 1 wherein the step of updating said examination image comprises fusing said examination image with at least one further examination image.

16. A method as claimed in claim 15 comprising fusing said examination image with at least one further examination image obtained with a different examination apparatus.

17. A method as claimed in claim 1 wherein the step of updating said examination image comprises effecting a transformation image selected from the group consisting of changing a size of the examination image, rotating said examination image, mirroring said examination image, and shifting said examination image.

18. A method as claimed in claim 1 comprising representing said updated examination image at said image reproduction device dependent on updating of at least one other examination image.

19. A method as claimed in claim 1 comprising associating said examination image with a billing code dependent on said comparison result.

20. A method as claimed in claim 1 comprising, in said computer, comparing said at least one item of image information of the examination image with at least one item of subject-specific information of the whole-body coordinate system using rules stored in a storage unit accessible by said computer.

21. A method as claimed in claim 20 comprising emitting a user prompt dependent on said comparison result.

22. A method as claimed in claim 1 comprising allowing revision of said updating of said examination image by interaction of a user through said computer.

23. A method as claimed in claim 22 comprising, in said computer, before permitting said revision of said updating of said examination image, requiring an entry by said user that allows said computer to establish user rights associated with the user.

24. A method as claimed in claim 1 comprising allowing revision of the representation of the examination image at said image reproduction device by interaction by a user through said computer.

25. A method as claimed in claim 24 comprising, in said computer, before permitting said revision of said updating of said examination image, requiring an entry by said user that allows said computer to establish user rights associated with the user.

26. A method as claimed in claim 1 wherein said computer comprises a plurality of modules, and comprising processing said updated examination image for representation at said image reproduction device in one of said modules that is different from at least one of said modules in which said computer obtains said comparison result.

27. An apparatus for representation and preparation of at least one examination image of an examination subject, comprising:
a medical imaging apparatus adapted to interact with an examination subject to obtain at least one examination image thereof;
a computer in communication with said medical imaging apparatus to receive said examination image therefrom;
said computer automatically specifying a whole-body coordinate system with regard to the examination subject dependent on at least one item of subject-specific information, and automatically spatially arranging said examination image in the whole-body coordinate system dependent on said subject-specific information to obtain a spatially-arranged examination image, and checking for consistency between said subject-specific information and said spatially arranged examination image by comparing at least one item of image information representing a feature depicted in the examination image with said at least one item of subject-specific information of the whole-body coordinate system, to obtain a comparison result that indicates whether an inconsistency exists between said item of image information and said at least one item of subject-specific information, and automatically updating said examination image dependent on said comparison result when said comparison result indicates said inconsistency, to remove said inconsistency; and
an image reproduction device in communication with said computer at which said computer causes said updated examination image to be represented.

* * * * *